(12) United States Patent
Canham et al.

(10) Patent No.: US 8,128,912 B2
(45) Date of Patent: Mar. 6, 2012

(54) METHOD OF PROTECTING SKIN FROM UV RADIATION USING A DERMATOLOGICAL COMPOSITION HAVING POROUS SILICON

(75) Inventors: Leigh T Canham, Malvern (GB); Roger Aston, Malvern (GB)

(73) Assignee: pSIMEDICA Limited, Malvern, Worcestershire (GB)

( * ) Notice: Subject to any disclaimer, the term of this patent is extended or adjusted under 35 U.S.C. 154(b) by 1225 days.

(21) Appl. No.: 11/142,332

(22) Filed: Jun. 2, 2005

(65) Prior Publication Data

US 2005/0226901 A1  Oct. 13, 2005

Related U.S. Application Data

(62) Division of application No. 10/344,153, filed as application No. PCT/GB01/03633 on Aug. 15, 2001, now abandoned.

(30) Foreign Application Priority Data

Aug. 18, 2000 (GB) .................................. 0020276.2

(51) Int. Cl.
*A61Q 17/04* (2006.01)
*A61K 8/00* (2006.01)
*A61K 8/02* (2006.01)
*A61K 8/18* (2006.01)
*A61K 8/25* (2006.01)

(52) U.S. Cl. ............ 424/59; 424/401; 514/63; 514/770; 514/844; 514/951

(58) Field of Classification Search .................. 424/489, 424/49, 401; 514/63, 770, 844, 951
See application file for complete search history.

(56) References Cited

U.S. PATENT DOCUMENTS

| 4,096,254 | A | | 6/1978 | Benson et al. |
| 4,529,593 | A | | 7/1985 | Warrell, Jr. et al. |
| 5,433,214 | A | | 7/1995 | Brehm et al. |
| 5,904,918 | A | * | 5/1999 | Sterphone et al. .............. 424/69 |
| 6,322,895 | B1 | * | 11/2001 | Canham ........................ 428/450 |
| 7,186,267 | B2 | * | 3/2007 | Aston et al. ................ 623/16.11 |

FOREIGN PATENT DOCUMENTS

| EP | 0 056 094 | | 7/1982 |
| EP | 0 875 538 | | 11/1998 |
| JP | 09-263517 | | 10/1997 |
| WO | WO 97/06101 | | 2/1997 |
| WO | WO 00/65347 | | 11/2000 |
| WO | WO 00/66190 | | 11/2000 |
| WO | WO 01/28529 | | 4/2001 |
| WO | WO 01/95952 | * | 12/2001 |

OTHER PUBLICATIONS

Matsueda et al., Preventing Makeup Darkening During Usage, 1996, Cosmetic and Toiletries Magazine, 111, pp. 35-40.*
Anglin et al., Porous Silicon in drug delivery devices and materials, pp. 1266-1277, 2008.*
Canham, Properties of Porous Silicon, 1997 pp. iii-xviii, 341, and 343-363.*
Porous Silicon as a Biomaterial, 2001, <http://www.azom.com/details.asp?ArticleID=529>.*
Matsueda and Ogihara, "Preventing Makeup Darkening During Usage", Cosmetics & Toiletries Magazine 111:35-40 (1996).
English translation of Office Action in JP 2002-520773 received Sep. 30, 2011.

* cited by examiner

*Primary Examiner* — James H. Alstrum-Acevedo
(74) *Attorney, Agent, or Firm* — Nixon & Vanderhye P.C.

(57) ABSTRACT

Dermatological methods of cosmetic, therapeutic, prophylactic, and/or diagnostic treatment by topically applying compositions comprising a multiplicity of particles, at least one of the particles comprising porous and/or polycrystalline silicon. Included are methods and compositions for sun protection applications. The use of porous silicon, polycrystalline silicon, and porous silicon oxide mirrors is disclosed.

7 Claims, 13 Drawing Sheets

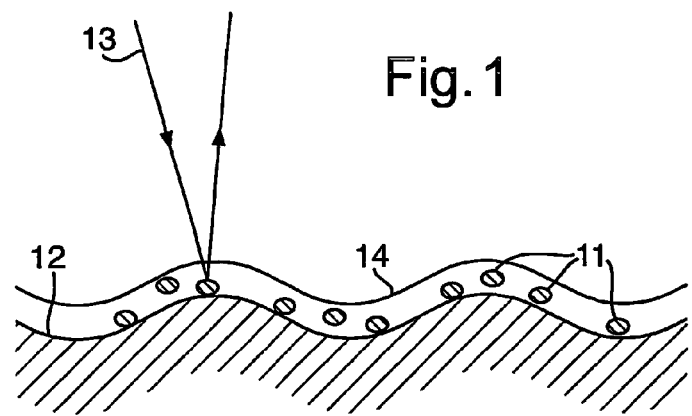
Fig. 1
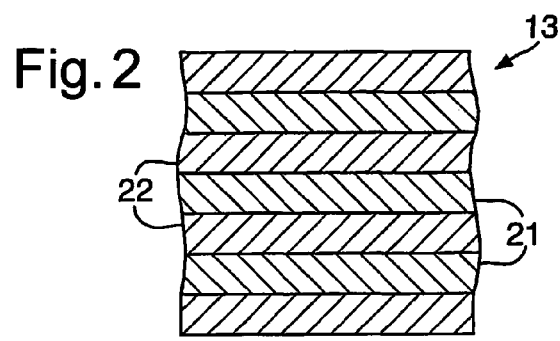
Fig. 2
Fig. 4
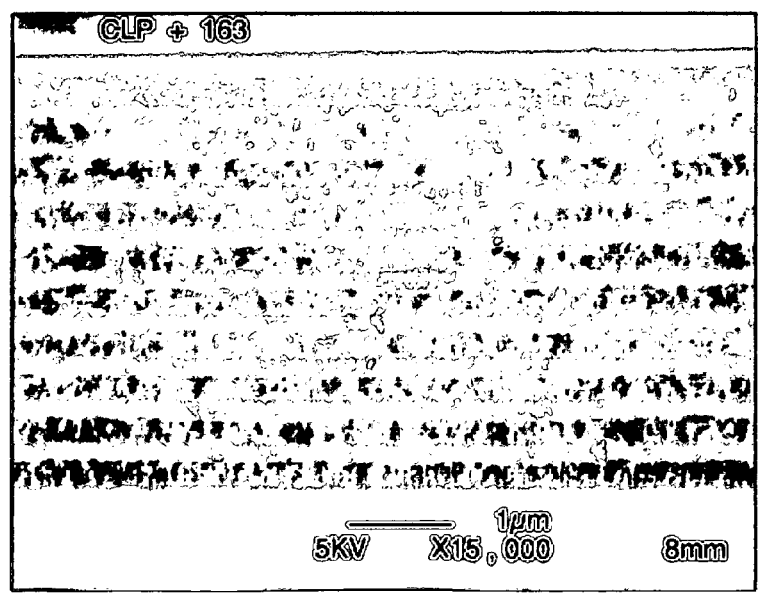

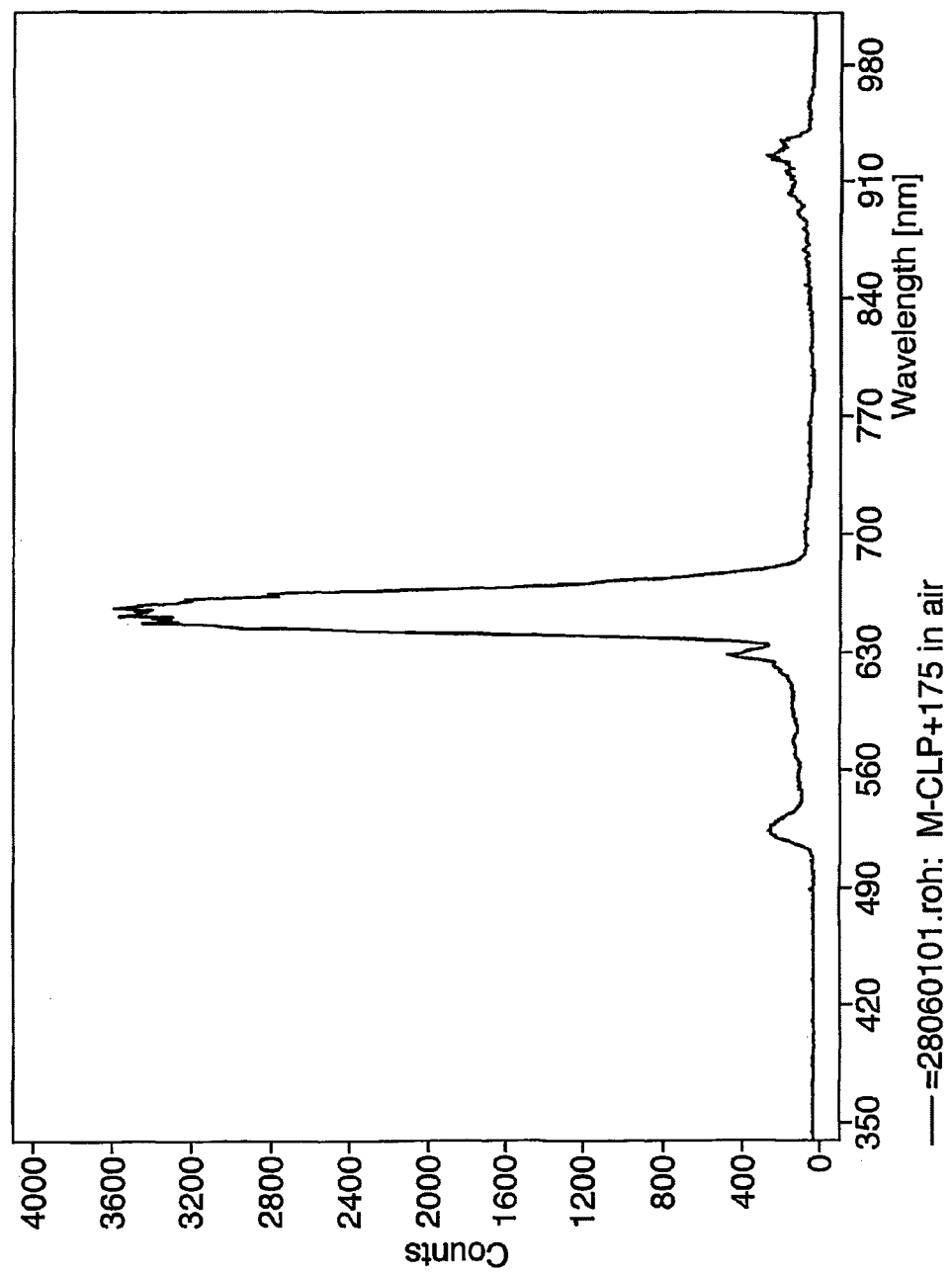

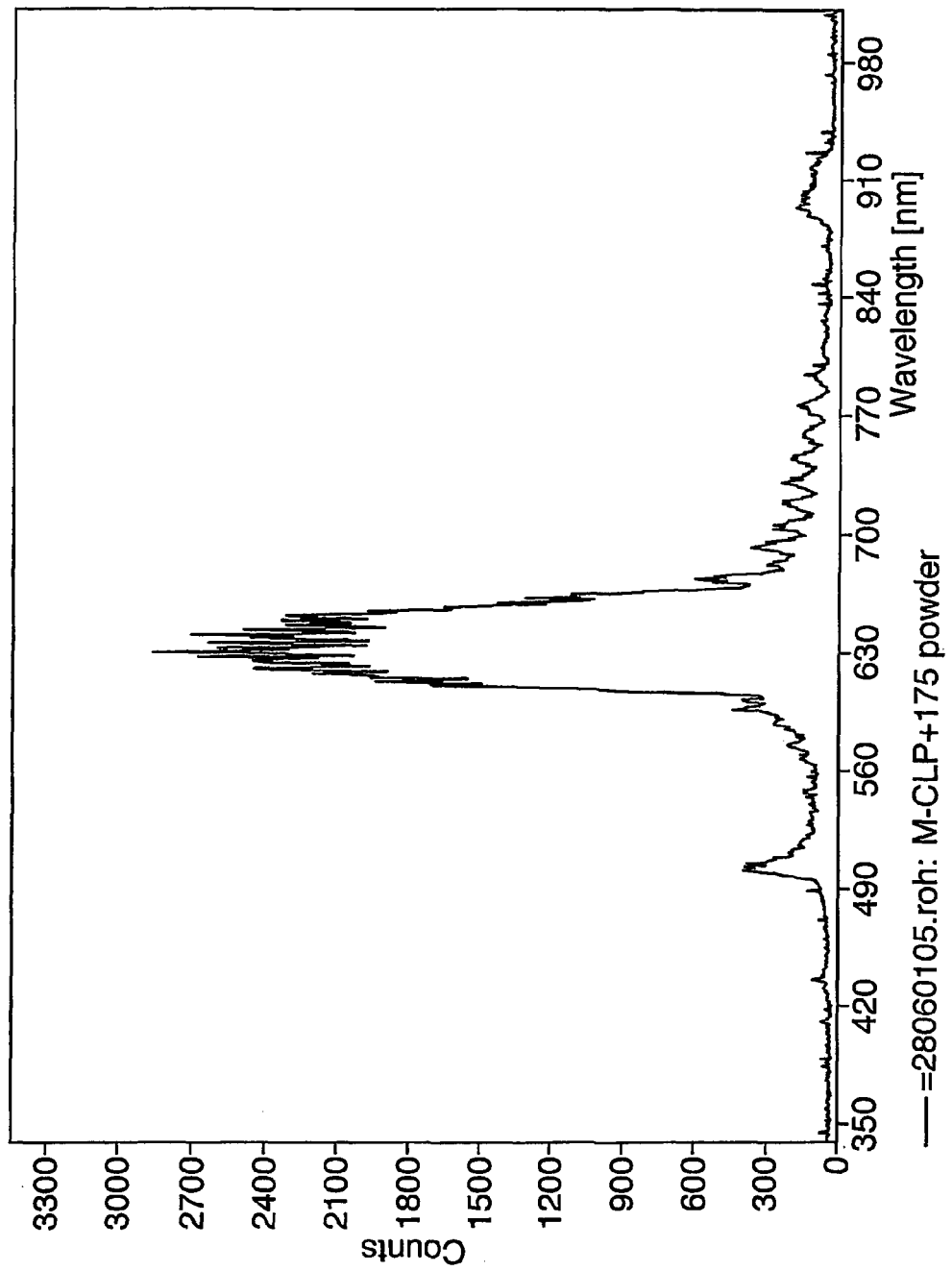

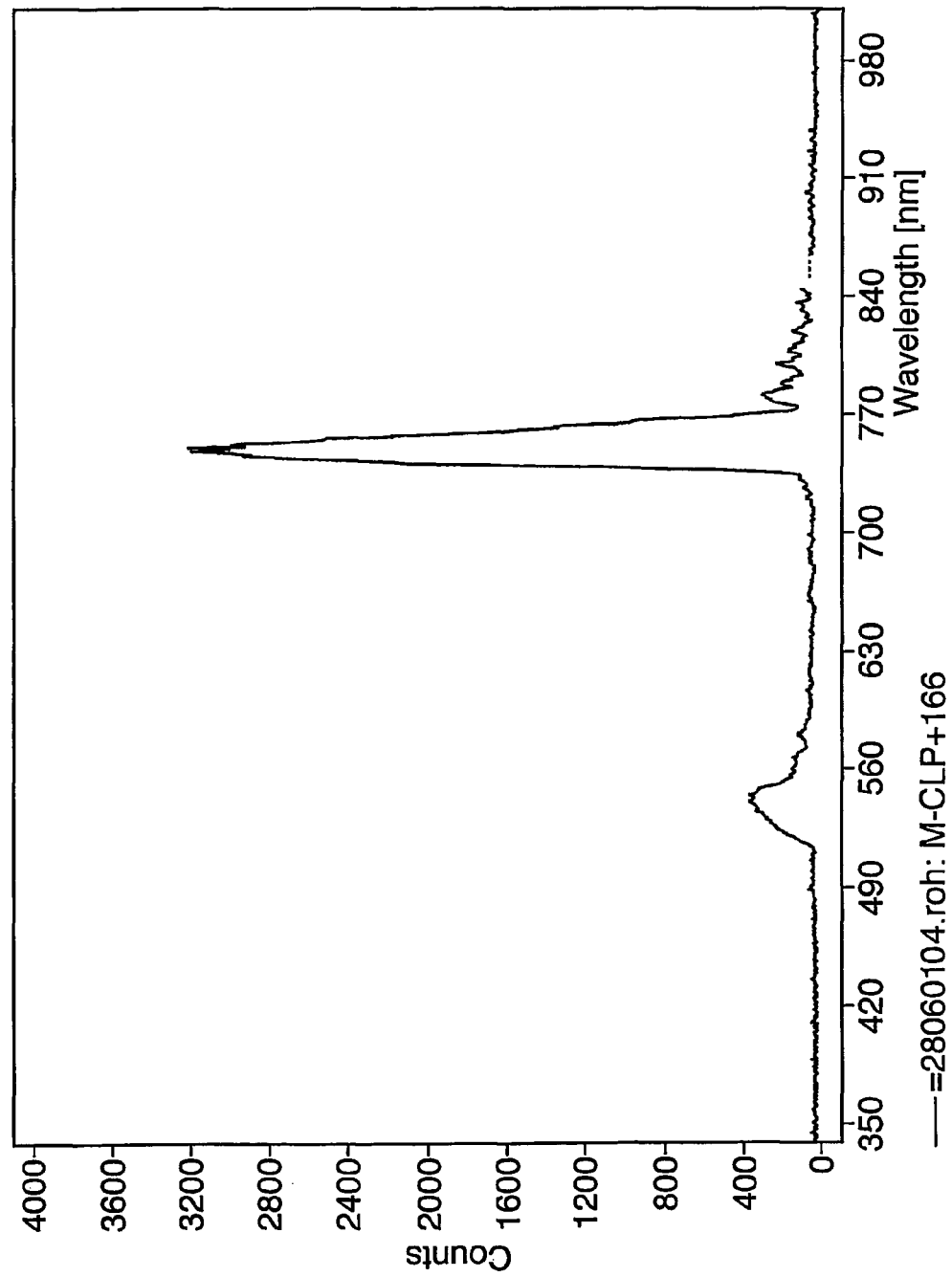

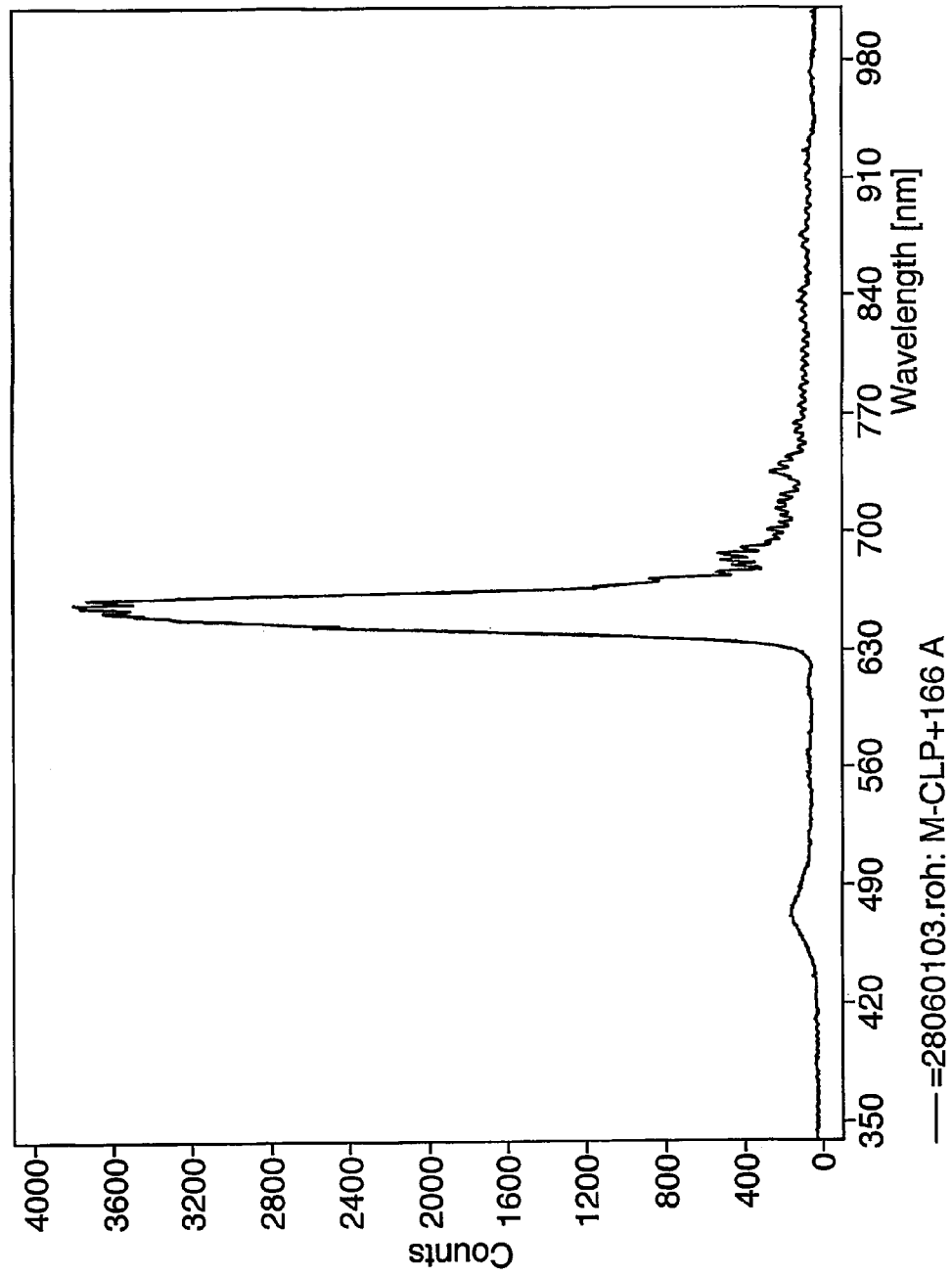

Fig. 9b
Spectrum 1. CLP+166; TTO+Gel top 1μm, 5keV SATW.
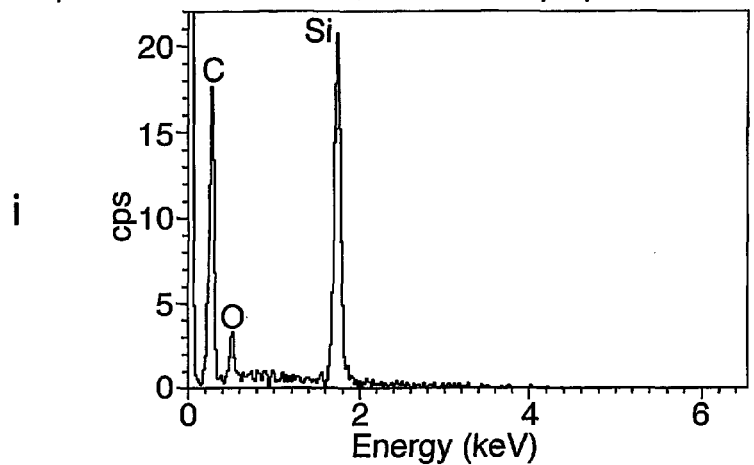
i
Spectrum 2. CLP+166; TTO+Gel Middle, 5keV SATW.
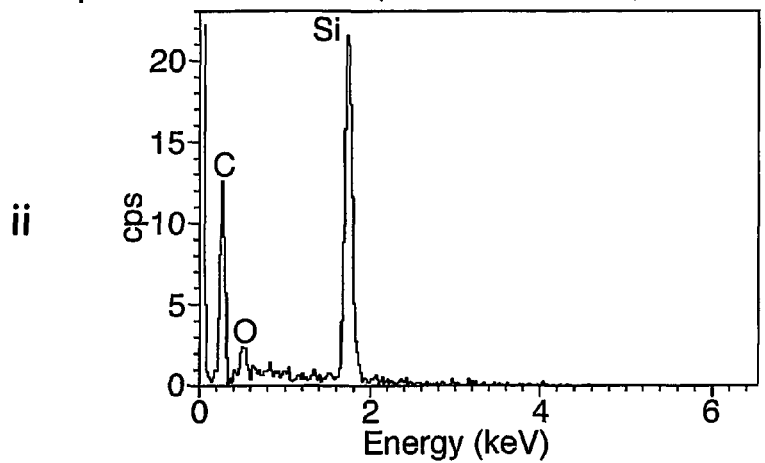
ii
Spectrum 3. CLP+166; TTO+Gel Bottom, 5keV SATW.
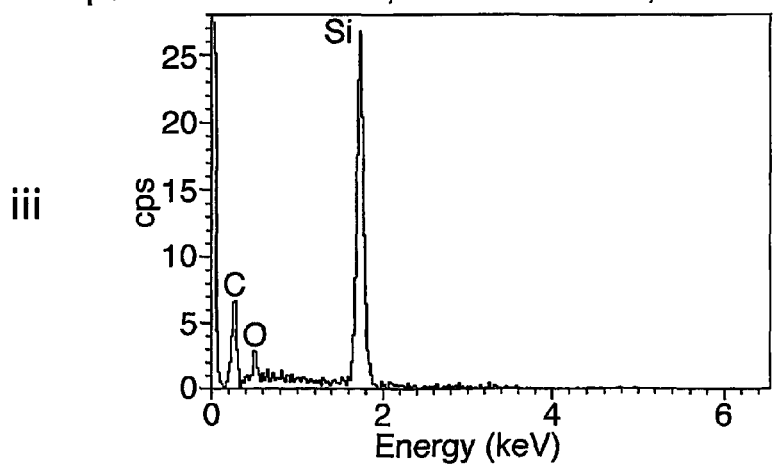
iii

METHOD OF PROTECTING SKIN FROM UV RADIATION USING A DERMATOLOGICAL COMPOSITION HAVING POROUS SILICON

CROSS REFERENCE TO RELATED APPLICATIONS

This application is a divisional of application Ser. No. 10/344,153 filed Feb. 10, 2003 now abandoned which in turn is a U.S. national phase of PCT/GB01/03633 filed Aug. 15, 2001, the entire content of each of which is hereby incorporated by reference in this application.

This invention relates to a new dermatological composition. More specifically this invention relates to a new dermatological composition comprising silicon and/or silicon oxide.

The term "dermatological composition" covers a huge range of products that may be applied to the skin. Such products may be used for the treatment of skin conditions or damaged skin; they may be used to protect the skin, or for cosmetic purposes; they may even be used to treat organs located beneath the skin.

Dermatological compositions are applied to skin in a number of different forms including creams, pastes, powders, and gels, and may include components such as oils, pigments, fillers, surfactants, emollients, basifying/acidifying agents, fragrances, pharmaceutical products, and particulates.

Particulates may be used in dermatological compositions for a variety of reasons. They may be present as a filler, which increases the volume of the skin composition. Fillers commonly used in skin creams include talc, mica, and silica. Alternatively the particulate may confer colour to the cream, say for cosmetic purposes. The particulate may be a beneficial substance that protects or has a beneficial effect upon the skin, or that has a beneficial effect on organs lying below the skin. Finally the particulate may be a carrier that interacts with a beneficial substance in such a manner that the effect of the beneficial substance is enhanced as a result of the interaction. For example a carrier may assist in transfer of a beneficial substance through or into the skin, or it may protect a beneficial substance from other components in the composition.

As is well known exposure to direct sunlight may cause sun-burn, ageing effects, and skin cancer. Cosmetic sunscreen preparations aim to reduce this risk and often include chemical compounds which are capable of absorbing certain wavelengths of UV radiation. Many also incorporate a particulate component having diameters of 10-150 nm whose purpose is to reflect or scatter certain wavelengths of UV radiation while remaining optically transparent on the skin. Although effective, UV absorbing chemicals may cause sensitisation in some users. The small particles used are typically of a metal oxide, with titanium and zinc oxides being particularly common.

A problem associated with the use of titanium dioxide is that it has a relatively high refractive index, which causes whitening when applied to the skin. To overcome this problem ultrafine particles of titanium dioxide have been used, which cause less scattering in the visible region. Unfortunately such ultrafine particles (of titanium oxide, or zinc oxide) suffer from problems of coagulation which can cause deterioration of their optical properties. A further problem associated with titanium and zinc oxides is their hydrophilicity, reducing the water repellent properties of any composition of which they form a part.

Dermatological compositions often have to satisfy a number of criteria such as cosmetic appearance, water resistance, and stability. The composition should be comfortable to apply and continue to feel comfortable once applied, for example it should not cause an allergic reaction and should not cause sensitisation of the skin.

The property of stability (the retention of the physical and chemical properties of the composition after manufacture) includes stability prior to and after application to the skin. A common cause of composition instability is the agglomeration of one or more of the components. Agglomeration of a solid component, comprising for example nanoparticles, may result in an abrasive or unpleasant sensation when the composition is applied to the skin.

There are thus many problems, or potential problems, to be taken into account when selecting products for topical application to human skin; and it is an objective of this invention to provide a new dermatological composition that ameliorates at least some of these problems.

According to a first aspect, the present invention provides a dermatological composition comprising a multiplicity of dermatological particles, at least one of the dermatological particles comprising porous and/or polycrystalline silicon.

Preferably the dermatological composition comprises a multiplicity of silicon particles each silicon particle comprising one or more of: bulk crystalline silicon, porous silicon, amorphous silicon, and polycrystalline silicon.

Porous and/or polycrystalline silicon, when located in a mammalian body, may be degraded to yield silicic acid, $H_4SiO_4$. Clinical evidence suggests that exposure to silicic acid is of value in the treatment of skin complaints such as psoriasis and conditions associated with the biological ageing of the skin, hair and nails. For example, studies by Lassus, in the Journal of International Medical Research, 1997, vol. 25, pp. 206-209 and 1993, vol. 21, pp. 209-215, discuss the results of tests involving the oral and topical administration of colloidal silicic acid to groups of patients. Significant improvements were observed in skin thickness and turgor; alleviation of the symptoms of chronic plaque-type psoriasis was also observed.

The effects of supplementing the diets of calves with silicic acid, $H_4SiO_4$, has been reported by Colomme et al., Biological Trace Element Research, 1997 vol. 56, p153. A 4.9% increase in dietary silicon over a 23 week period led to a 70% increase in serum silicon concentration and produced a significant increase in dermal collagen levels.

The present invention, therefore provides a composition which is suited for use as a pharmaceutical product to deliver silicic acid via the skin. The compostion is suitable for use as a treatment for conditions affecting the skin, such as psoriasis and also those which affect the underlying bones and joints, such as osteoporosis.

Thin films of porous silicon show good optical transparency, for example a 20 μm thick film with porosity of 90% provides greater than 95% transmission in the visible region. Furthermore, the absorption of UV radiation by porous silicon is high, for example the absorption coefficient above the direct bandgap of Si (3.25 eV or 400 nm) is around $5 \times 10^4$ $cm^{-1}$ for a material with a porosity of 90%. This far exceeds the UV absorption ability of commonly used metal oxide nanoparticles such as $TiO_2$ which has an absorption coefficient of ca. $10^3$ $cm^{-1}$ at 400 nm. Porous silicon is therefore suitable for use as a UV radiation screening agent in a sunscreen preparation.

The dermatological composition may further comprise a dermatologically acceptable carrier. Preferably the dermatological carrier comprises a natural or synthetic fat; the fat may be an oil or a wax.

High porosity porous silicon has a refractive index comparable to many commonly used dermatological carriers, making its concealment by the carrier more effective.

The dermatological composition may comprise one or more of: a fatty binder, a filler, a pigment, a volatile oil, an anti-oxidant, a surfactant, a basifying agent, an acidifying agent, and a fragrance.

The dermatological composition may have a composition such that it is one of: a cream, a lotion, a topical solution, a paste, a linament, a powder, a gel, a tincture, and an aerosol.

For pharmaceutical use small quantities of porous and/or polycrystalline silicon may be effective. Porous and/or polycrystalline silicon may comprise less than 2% by weight with respect to the total weight of the composition. Preferably, the porous and/or polycrystalline silicon comprises at least 2% by weight with respect to the total weight of the composition.

Suitably the or each porous and/or polycrystalline silicon particle has a particle size in the range from 0.01 to 250 μm, preferably, the particle size is in the range from 0.01 to 0.15 μm and more preferably the particle size is in the range from 0.01 to 0.03 μm.

Advantageously the dermatological composition comprises a multiplicity of silicon particles and each silicon particle has a particle size in the range from 0.01 to 250 μm. More advantageously, each silicon particle has a particle size in the range from 0.01 to 0.15 μm. Yet more advantageously each silicon particle has a particle size is in the range from 0.01 to 0.03 μm.

The particle size range chosen is dependent on the intended use of the composition. For use in a sunscreen applications, it may be desirable for the particles to have a size that scatters ultraviolet wavelengths. The upper bound to the particle size of the porous silicon is limited by the need for the composition to be comfortable in use. Particles which are too large will result in the composition being granular to the touch and which may cause abrasion of the skin on application. The dermatological composition may be used as a deoderant. The dermatological composition may also be used as a coloured, lipstick. Finally, cosmetic aspects may also have to be taken into account, the particle size influencing the appearance of the composition on the skin.

The extent of porosity of the porous silicon has been shown by the inventors to affect the rate at which it is absorbed by the mammalian body. Highly porous silicon is more rapidly resorbed than lower porosity silicon. The porosity is measured in terms of the fractional void content of the porous silicon.

Preferably, the dermatological composition comprises porous silicon and the porous silicon has a porosity of at least 1%, more preferably, the porous silicon has a porosity of at least 50%.

Porous silicon may be classified according to the nature of the porosity. Dependent on the conditions of manufacture, it may be microporous, with an average pore size of less than 20 Å; mesoporous, with an average pore size of between 20 and 500 Å; or macroporous with an average pore size of greater than 500 Å.

For use in the present invention, preferably the dermatological composition comprises porous silicon and the porous silicon is microporous or mesoporous, more preferably it is mesoporous.

Preferably the porous and/or polycrystalline silicon is resorbable.

Advantageously the dermatological composition further comprises at least one beneficial substance.

For the purposes of this specification a beneficial substance is defined as a substance that has a beneficial effect when administered to the body of an animal or human. The beneficial substance may be located within the structure of the porous and/or polycrystalline silicon. If the beneficial substance is resorbable, then corrosion of the porous and/or polycrystalline silicon may result in release of the beneficial substance.

The beneficial substance may be one or more of: a pharmaceutical material, a biological material, a genetic material, a radioactive material, an antibacterial agent or a luminescent material.

The beneficial substance may be one or more of: insulin, lidocaine, alprostadil, calcitonin, DNA, RNA, tumour necrosis factor (TNS), a peptide, cytokine, a hormone, an antibody, a cytotoxic agent, an adjuvant, a steroid, an antibiotic, a cinamate derivative, octyl methoxycinnamate, a Salicylate, a benzophenone, an anthranilate, a dibenzoylmethane, a p-aminobenzoate, a vitamin C derivative, a β carotene, an α tocopherol, a thiol, an antifungal agent, an antiviral agent, and a psoralen.

Another beneficial substance may be a protein, for example collagen. It is reputed that collagen has anti-ageing attributes when applied to the skin. A further beneficial substance may be a vitamin, for example vitamin E. A yet further beneficial substance may be a trace mineral. A non-exhaustive list of suitable trace minerals includes; selenium, manganese, molybdenum, chromium, vanadium, iodine, fluorine and cobalt.

In general, trace minerals are needed by the body only in very small quantities, the recommended daily allowance (RDA) of certain trace elements can be less than 0.1 mg/day. The effects of deficiencies are however, well documented. Furthermore, some trace minerals are required in specific areas of the body. Delivery of trace minerals in the form of a topical application is therefore attractive.

A still further beneficial substance may be a therapeutic element. Possible therapeutic elements include, lithium, gold, silver, copper, zinc, and platinum. These elements have widespread clinical usage for the treatment of chronic conditions; lithium is used to treat depression, silver and gold have antibacterial properties, copper and zinc are commonly applied via the skin, and platinum is used in the treatment of neoplastic diseases. It may also be desirable to be able to deliver these elements to specific sites via topical application.

It is of course intended that the porous silicon may have more than one beneficial substance incorporated within its structure.

Preferably the dermatological composition comprises derivatised porous silicon. For the purposes of this specification derivatised porous silicon is defined as porous silicon having a monomolecular, or monatomic layer that is chemically bonded to at least part of the surface, including the surface of the pores, of the porous silicon. The chemical bonding, between the layer and the silicon, may comprise a Si—C and/or Si—O—C bonding.

In this way the beneficial substance may be bonded to the surface of the porous silicon. The porous silicon may also be derivatised so as to enhance wetting of the porous and/or polycrystalline silicon particles by other components contained in the dermatological composition.

Advantageously the dermatological composition comprises silicon oxide, more advantageously the dermatological composition comprises porous and/or polycrystalline silicon oxide. Yet more advantageously the dermatological composition comprises porous silicon part of which has been oxidised to form silicon oxide.

The dermatological composition may comprise a multiplicity of mirrors, each mirror comprising a plurality of layers, each layer comprising porous and/or polycrystalline silicon.

By having a plurality of porous layers, each layer having a different porosity to layer(s) adjacent to it, and by controlling the porosity of each layer, the mirror may be made to reflect radiation over a limited range of wavelengths. The dermatological composition may comprise a first group of mirrors that reflect radiation over a first wavelength range, and a second group of mirrors that reflect radiation over a second wavelength range. The dermatological composition may comprise several groups of mirrors, each group reflecting radiation over a wavelength range that differs from that of the other groups.

The use of mirrors that reflect different wavelengths may have two advantages. Firstly it potentially affords protection over a greater range of wavelengths. Secondly it opens the way for coloration of the composition using the reflective properties of the mirrors; in this way the composition may be used to darken the skin causing it to appear tanned.

Preferably each mirror may have a largest dimension in the range 50 nm to 2 mm. More preferably each mirror has a largest dimension between 100 nm and 1 mm.

Each mirror may have a largest dimension that is greater than twice its smallest dimension.

Advantageously each mirror comprises resorbable porous silicon.

The mirrors may reflect electromagnetic radiation away from the skin of a human to which the dermatological composition has been applied. If each mirror is resorbable then they will gradually corrode upon application to the skin. This corrosion will be linked to a change in the appearance of the composition, and this change can be used as an indicator of the composition effectiveness.

Preferably the or each dermatological particle comprises silicon oxide.

According to a second aspect the invention provides a dermatological composition comprising a multiplicity of silicon oxide mirrors, each silicon oxide mirror comprising a plurality of layers, each layer comprising porous and/or polycrystalline silicon oxide.

By having a plurality of porous layers, each layer having a different porosity to layer(s) adjacent to it, and by controlling the porosity of each layer, the mirror may be made to reflect radiation over a limited range of wavelengths. The dermatological composition may comprise a first group of mirrors that reflect radiation over first wavelength range, and a second group of mirrors that reflect radiation over a second wavelength range. The dermatological composition may comprise several groups of mirrors, each group reflecting radiation over a wavelength range that differs from that of the other groups.

Preferably each silicon oxide mirror may have a largest dimension in the range 50 nm to 2 mm. More preferably each silicon oxide mirror has a dimension between 100 nm and 1 mm.

Each mirror may have a largest dimension that is greater than twice its smallest dimension.

The dermatological composition may further comprise a dermatologically acceptable carrier. Preferably the dermatological carrier comprises a natural or synthetic fat; the fat may be an oil or a wax.

Porous silicon oxide has a refractive index comparable to that of commonly used dermatologiocal carriers, making its concealment by the carrier more effective.

Preferably the porous silicon oxide is resorbable.

The dermatological composition may comprise one or more of: a fatty binder, a filler, a pigment, a volatile oil, an anti-oxidant, a surfactant, and a fragrance.

The dermatological composition may have a composition such that it is one of a cream, a lotion, a topical solution, a paste, a linament, a powder, a gel, a tincture or an aerosol.

According to a third aspect the invention provides a method of therapeutic or prophylactic treatment of a human or animal body comprising the steps of: topically applying a dermatological composition and allowing the dermatological composition to treat the human or animal; the dermatological composition comprising a multiplicity of dermatological particles, at least one of the dermatological particles comprising porous and/or polycrystalline silicon.

According to a fourth aspect the invention provides a method of cosmetic treatment of a human or animal body comprising the steps of: topically applying a dermatological composition and allowing the dermatological composition to cosmetically treat the human or animal; the dermatological composition comprising a multiplicity of dermatological particles, at least one of the dermatological particles comprising porous and/or polycrystalline silicon.

According to a fifth aspect the invention provides a method of therapeutic or prophylactic treatment of a human or animal body comprising the steps of: topically applying a dermatological composition and allowing the dermatological composition to treat the human or animal; the dermatological composition comprising a multiplicity of silicon mirrors, at least one of the mirrors comprising a plurality of porous and/or polycrystalline silicon oxide layers, each layer having a different refractive index to the layer or layers adjacent to it.

According to a sixth aspect the invention provides a method of cosmetic treatment of a human or animal body comprising the steps of: topically applying a dermatological composition and allowing the dermatological composition to cosmetically treat the human or animal; the dermatological composition comprising a multiplicity of mirrors, at least one of the mirrors comprising a plurality of layers of porous and/or polycrystalline silicon oxide, each layer having a refractive index that differs from that of the layer or layers adjacent to it.

According to a seventh aspect the invention provides a method of manufacturing a dermatological composition comprising the step of combining at least one particle, comprising porous and/or polycrystalline silicon, with a dermatologically acceptable carrier.

According to a eighth aspect the invention provides a method of manufacturing a dermatological composition comprising the step of combining at least one mirror, the mirror comprising a plurality of layers of porous and/or polycrystalline silicon oxide each layer having a refractive index that differs from that of the layer or layers adjacent to it, with a dermatologically acceptable carrier.

According to a ninth aspect, the invention provides a method of protecting at least part of an animal or human from electromagnetic radiation, comprising the steps:
  (a) applying a dermatological composition to at least part of the skin of the animal or human; and
  (b) allowing, when at least part of the skin is exposed to electromagnetic radiation, the dermatological composition to reflect at least part of the electromagnetic radiation;
wherein step (b) comprises the step of reflecting at least part of the electromagnetic radiation by means of a multiplicity dermatological mirrors.

Each dermatological mirror may comprise a plurality of porous silicon and/or porous silicon oxide layers. Each porous silicon and/or porous silicon oxide layer may have a different porosity to that of its neighbouring layer or layers. Each dermatological mirror may comprise a plurality of porous silicon and/or porous silicon oxide layers having alternating high and low porosities. The low porosity layers may each have a porosity between 25% and 65%, and the high porosity layers may each have a porosity between 60% and 95%. Each dermatological mirror may comprise greater than 10 layers. Each dermatological mirror may comprise greater than 100 layers. Each dermatological mirror may comprise greater than 200 layers. Each dermatological mirror may comprise greater than or equal to 400 layers.

Each layer of porous silicon and/or porous silicon oxide, from which the mirrors may be formed, has a different refractive index to its neighbouring layer or layers, the combined layers forming a Bragg stack mirror.

The dermatological composition may comprise a dermatologically acceptable carrier such as a natural or synthetic fat. The multiplicity of dermatological mirrors may be in the form of a powder, the powder being distributed throughout the carrier.

Preferably each dermatological mirror comprises one or more of: bulk crystalline silicon, porous silicon, amorphous silicon, and polycrystalline silicon.

Advantageously each dermatological mirror comprises silicon oxide.

The dermatological composition may be a sun cream, providing protection against ultraviolet radiation.

Each dermatological mirror may comprise, porous silicon, and at least part of the porous silicon may comprise porous polycrystalline and/or amorphous silicon.

Step (b) may comprise the step of allowing the multiplicity of dermatological mirrors to reflect, with a reflectivity peak between 5 nm and 380 nm, at least part of the electromagnetic radiation.

Step (b) may comprise the step of allowing the multiplicity of dermatological mirrors to reflect, with a reflectivity peak between 380 nm and 780 nm, at least part of the electromagnetic radiation.

Step (b) may comprise the step of allowing the multiplicity of dermatological mirrors to reflect, with a reflectivity peak between 740 nm and 100 µm, at least part of the electromagnetic radiation.

Step (b) may comprise the step of allowing the multiplicity of dermatological mirrors to reflect, with a reflectivity peak between 400 nm and 800 nm, at least part of the electromagnetic radiation.

Step (b) may comprise the step of allowing the multiplicity of dermatological mirrors to reflect, with a reflectivity peak between 550 nm and 700 nm, at least part of the electromagnetic radiation.

Preferably the average particle size of the multiplicity of dermatological mirrors is in the range 50 nm to 2 mm. More preferably the average size of the multiplicity of the dermatological mirrors is between 100 nm and 1 mm.

The average particle size of the multiplicity of dermatological mirrors may be in the range 10 nm to 50 microns. The average particle size of the multiplicity of dermatological mirrors may be in the range 200 microns to 1 mm.

The reflectance properties of the multiplicity of dermatological mirrors may impart colour to the dermatological composition, or they can be used to reflect undesirable radiation from the skin to which the composition is applied.

According to a tenth aspect, the invention provides a dermatological composition comprising a plurality of dermatological mirrors.

Each dermatological mirror may comprise a plurality of porous silicon and/or porous silicon oxide layers. Each porous silicon and/or silicon oxide layer may have a different porosity to that of its neighbouring layer or layers. Each dermatological mirror may comprise a plurality of porous silicon and/or porous silicon oxide layers having alternating high and low porosities. The low porosity layers may each have a porosity between 25% and 65%, and the high porosity layers may each have a porosity between 60% and 95%. Each dermatological mirror may comprise greater than 10 layers. Each dermatological mirror may comprise greater than 100 layers. Each dermatological mirror may comprise greater than 200 layers. Each dermatological mirror may comprise greater than or equal to 400 layers.

The dermatological composition may be a sun-cream.

Preferably each dermatological mirror comprises one or more of: bulk crystalline silicon, porous silicon, amorphous silicon, and polycrystalline silicon.

Each dermatological mirror may comprise silicon oxide. Each dermatological mirror may comprise porous silicon oxide.

Each dermatological mirror may comprise porous silicon, and the porous silicon may comprise porous polycrystalline and/or porous amorphous silicon.

Preferably the dermatological composition comprises a dermatologically acceptable carrier. Advantageously the dermatological carrier may comprise a natural or synthetic fat such as an oil or wax. The plurality of dermatological mirrors may be distributed substantially uniformly throughout the volume of the dermatological carrier.

The orientation of each dermatological mirror may be substantially random.

Each dermatological mirror may comprise porous silicon and/or porous silicon oxide, the porous silicon and/or porous silicon oxide having a structure such that, when each dermatological mirror is substantially randomly oriented, the plurality of dermatological mirrors has a peak in its reflectivity spectrum between 100 nm and 380 nm.

Each dermatological mirror may comprise porous silicon and/or porous silicon oxide, the porous silicon and/or porous silicon oxide having a structure such that, when each dermatological mirror is substantially randomly oriented, the plurality of dermatological mirrors has a peak in its reflectivity spectrum between 380 nm and 780 nm.

Each dermatological mirror may comprise porous silicon and/or porous silicon oxide, the porous silicon and/or porous silicon oxide having a structure such that, when each dermatological mirror is substantially randomly oriented, the plurality of dermatological mirrors has a peak in its reflectivity spectrum between 740 nm and 100 µm.

Each dermatological mirror may comprise porous silicon and/or porous silicon oxide, the porous silicon and/or porous silicon oxide having a structure such that, when each dermatological mirror is substantially randomly oriented, the plurality of dermatological mirrors has a peak in its reflectivity spectrum between 400 nm and 800 nm.

Each dermatological mirror may comprise porous silicon and/or porous silicon oxide, the porous silicon and/or porous silicon oxide having a structure such that, when each dermatological mirror is substantially randomly oriented, the plurality of dermatological mirrors has a peak in its reflectivity spectrum between 550 nm and 700 nm.

Each dermatological mirror may comprise porous silicon and/or porous silicon oxide, the porous silicon and/or porous silicon oxide having a structure such that, when each dermatological mirror is substantially randomly oriented, the plurality of dermatological mirrors has a peak in its reflectivity spectrum between 630 nm and 700 nm.

Each dermatological mirror may substantially consist of porous silicon.

Each dermatological mirror may substantially consist of porous silicon oxide.

Preferably the average particle size of the plurality of dermatological mirrors is in the range 50 nm to 2 mm. More preferably the average particle size of the plurality of the dermatological mirrors is between 100 nm and 1 mm.

The average size of the average particle size of the plurality of dermatological mirrors may be in the range 10 nm to 50 microns. The average size of the average particle size of the plurality of dermatological mirrors may be in the range 200 microns to 100 μm.

At least some of the dermatological mirrors may comprise silicon oxide having a structure such that it is soluble in human and/or animal sweat. At least some of the dermatological mirrors may comprise silicon oxide having a structure such that it is soluble in simulated human and/or animal sweat.

At least some of the dermatological mirrors may comprise silicon having a structure such that it is soluble in human and/or animal sweat. At least some of the dermatological mirrors may comprise silicon having a structure such that it is soluble in simulated human and/or animal sweat.

At least some of the dermatological mirrors may comprise a beneficial substance.

The corrosion of silicon and/or silicon oxide, which may form part of the dermatological composition, in sweat has several advantages. As mentioned above, dermatological mirrors may impart colour to the dermatological composition. Corrosion of the mirrors in sweat could therefore result in a colour change in the composition, a colour change that could be used to monitor the efficacy of the composition, and indicate the need for further application of the composition.

Advantageously the dermatological composition comprises a volatile material. The volatile material may comprise more than one compound. The volatile material may be a liquid or solid at 20 C and 760 mm Hg. Preferably the volatile material is a liquid at 20 C and 760 mm Hg. The volatile material may have a volatility such that, when 9 g±1 g is disposed within a layer of mesoporous silicon, the mass loss through evapouration at 20 C and 760 mm Hg is greater than or equal to 0.01 mg per minute over the first two minutes of measurement.

The volatile material may be lavender oil and/or Tea Tree Oil.

The dermatological mirrors may be of value in imparting a colour to the dermatological composition; they may even give the composition a glittering or glinting appearance. At least part of the volatile material may be distributed in or on the silicon and/or silicon oxide, from which the dermatological composition is at least partly formed.

Advantageously the silicon, from which the plurality of dermatological mirrors are at least partly formed, comprises porous silicon, and at least some of the volatile material is disposed in at least some of the pores of the porous silicon.

According to an eleventh aspect, the invention provides a method of delivering a beneficial substance to or through at least part of the skin of an animal or human, comprising the steps of:
(a) applying a dermatological composition, comprising a beneficial substance, to at least part of the skin of the animal or human; and
(b) allowing the beneficial substance to be released to or through the skin of the animal and/or human;

wherein the dermatologal composition comprise silicon and/or silicon oxide, at least part of the beneficial substance being located in or on at least part of the silicon and/or silicon oxide, and wherein step (b) comprises the step of allowing the silicon and/or silicon oxide to corrode in sweat excreted from the skin of the animal or human, thereby releasing the beneficial substance.

The dermatological composition may comprise silicon and the silicon may be selected from one or more of bulk crystalline silicon, porous silicon, amorphous silicon, and polycrystalline silicon. Preferably the dermatological composition comprises porous silicon.

The dermatological composition may comprise silicon oxide, and the silicon oxide may be porous silicon oxide.

The dermatological composition may comprise porous silicon and the porous silicon may be porous polycrystalline and/or amorphous silicon.

The dissolution of silicon and/or silicon oxide in sweat means that the beneficial substance associated with it may be released as a result of the dissolution.

The step of allowing the porous silicon and/pr silicon oxide to corrode may comprise the step of allowing the porous silicon and/or silicon oxide to corrode less than or equal to 2 hours after contact with the sweat.

The step of allowing the porous silicon and/or porous silicon oxide to corrode may comprise the step of allowing the porous silicon and/or silicon oxide to corrode less than or equal to 6 hours after contact with the sweat.

The beneficial substance may comprise silicon or a silicon compound. The beneficial substance may be formed, at least partly from at least some of the porous silicon.

The beneficial substance may be one or more of: a pharmaceutical material, a biological material, a genetic material, a radioactive material, an antibacterial agent or a luminescent material.

The beneficial substance may be one or more of: insulin, lidocaine, alprostadil, calcitonin, DNA, RNA, tumour necrosis factor (TNS), a peptide, cytokine, a hormone, an antibody, a cytotoxic agent, an adjuvant, a steroid, an antibiotic, a cinamate derivative, octyl methoxycinnamate, a Salicylate, a benzophenone, an anthranilate, a dibenzoylmethane, a p-aminobenzoate, a vitamin C derivative, a β carotene, an α tocopherol, a thiol, an antifungal agent, an antiviral agent, and a psoralen.

Another beneficial substance may be a protein, for example collagen. It is reputed that collagen has anti-ageing attributes when applied to the skin. A further beneficial substance may be a vitamin, for example vitamin E. A yet further beneficial substance may be a trace mineral. A non-exhaustive list of suitable trace minerals includes; selenium, manganese, molybdenum, chromium, vanadium, iodine, fluorine and cobalt.

A still further beneficial substance may be a therapeutic element. Possible therapeutic elements include, lithium, gold, silver, copper, zinc, and platinum.

The silicon, from which the dermatological composition may be at least partly formed, may comprise a multiplicity of silicon particles. At least some of the silicon particles may comprise porous-silicon.

The silicon oxide, from which the dermatological composition may at least partly be formed, may comprise a multiplicity or silicon oxide particles.

According to a twelfth aspect, the invention provides a dermatological composition comprising a multiplicity of porous silicon particles, each porous silicon particle comprising an outer layer; characterised in that the outer layer has a composition such that it corrodes, when it is placed in contact with the skin of an animal or human.

The outer layer may comprise gelatin.

According to an thirteenth aspect the invention provides a dermatological composition comprising a multiplicity of dermatological particles.

Preferably each dermatological particle comprises one or more of: bulk crystalline silicon, porous silicon, amorphous silicon, and polycrystalline silicon. More preferably each dermatological particle comprises porous silicon.

Certain forms of porous silicon, are photoluminescent, emitting visible light when illuminated with ultraviolet radiation. It may therefore be used as a marker to determine whether a beneficial substance has been administered by the application of a dermatological composition. Particles of small particles of porous silicon, invisible under normal conditions, may photoluminesce when the skin of an animal or human is exposed to the UV radiation.

Advantageously each dermatological particle comprises silicon oxide. More advantageously each silicon oxide particle comprises porous silicon oxide.

The dermatological composition may further comprise a dermatologically acceptable carrier. Preferably the dermatological carrier comprises a natural or synthetic fat; the fat may be an oil or a wax. The multiplicity of silicon and/or silicon oxide particles may be distributed throughout the carrier.

According to a fourteenth aspect, the invention provides the use of silicon and/or silicon oxide for the manufacture of a medicament for the delivery of a beneficial substance to or through at least part of the skin of an animal or human.

The step of delivering a beneficial substance to or through at least part of the skin, may comprise the steps of applying a dermatological composition, comprising the beneficial substance, to at least part of the skin of the animal or human and allowing the beneficial substance to be released to or through the skin of the animal and/or human.

The dermatological composition may comprise at least part of the silicon and/or silicon oxide.

At least part of the beneficial substance may be located in or on at least part of the silicon and/or silicon oxide and the step of allowing the beneficial substance to be released may comprise the step of allowing the silicon and/or silicon oxide to corrode in sweat excreted from the skin of the animal or human, thereby releasing the beneficial substance.

Silicon, used to deliver the beneficial substance, may be selected from one or more of bulk crystalline silicon, porous silicon, amorphous silicon, and polycrystalline silicon. Preferably the silicon comprises porous silicon.

Silicon oxide, used to deliver the beneficial substance, may be porous silicon oxide.

The dissolution of silicon and/or silicon oxide in sweat means that the beneficial substance associated with it may be released as a result of the dissolution.

The step of allowing the porous silicon and/or silicon oxide to corrode may comprise the step of allowing the porous silicon and/or silicon oxide to corrode less than or equal to 2 hours after contact with the sweat.

The step of allowing the porous silicon and/or porous silicon oxide to corrode may comprise the step of allowing the porous silicon and/or silicon oxide to corrode less than or equal to 6 hours after contact with the sweat.

The beneficial substance may comprise silicon or a silicon compound. The beneficial substance may be formed, at least partly from at least some of the porous silicon.

The beneficial substance may be one or more of: a pharmaceutical material, a biological material, a genetic material, a radioactive material, an antibacterial agent or a luminescent material.

The beneficial substance may be one or more of: insulin, lidocaine, aiprostadil, calcitonin, DNA, RNA, tumour necrosis factor (TNS), a peptide, cytokine, a hormone, an antibody, a cytotoxic agent, an adjuvant, a steroid, an antibiotic, a cinamate derivative, octyl methoxycinnamate, a Salicylate, a benzophenone, an anthranilate, a dibenzoylmethane, a p-aminobenzoate, a vitamin C derivative, a $\beta$ carotene, an $\alpha$ tocopherol, a thiol, an antifungal agent, an antiviral agent, and a psoralen.

Another beneficial substance may be a protein, for example collagen. It is reputed that collagen has anti-ageing attributes when applied to the skin. A further beneficial substance may be a vitamin, for example vitamin E. A yet further beneficial substance may be a trace mineral. A non-exhaustive list of suitable trace minerals includes; selenium, manganese, molybdenum, chromium, vanadium, iodine, fluorine and cobalt.

A still further beneficial substance may be a therapeutic element. Possible therapeutic elements include, lithium, gold, silver, copper, zinc, and platinum.

The silicon, from which the dermatological composition may be at least partly formed, may comprise a multiplicity of silicon particles. At least some of the silicon particles may comprise porous silicon.

The silicon oxide, from which the dermatological composition may at least partly be formed, may comprise a multiplicity or silicon oxide particles.

BRIEF DESCRIPTION OF THE DRAWINGS

The invention will now be described by way of example only with reference to the following drawings, in which:

FIG. 1 shows a dermatological composition, according to the invention, comprising a multiplicity of particles in contact with human skin;

FIG. 2 shows one of the particles illustrated in FIG. 1;

FIG. 4 shows an SEM image of a porous silicon mirror prior to immersion in simulated human sweat;

FIG. 7 shows reflectance spectra for porous silicon, which is in the form of a film, and also in the form of a powder;

FIG. 8 shows the effect of oxidation on the reflectance spectrum of porous silicon mirror;

FIG. 9b shows EDX plots for a gelatine coated porous silicon mirror;

PREPARATION OF A FIRST DERMATOLOGICAL COMPOSITION

Figure 3:
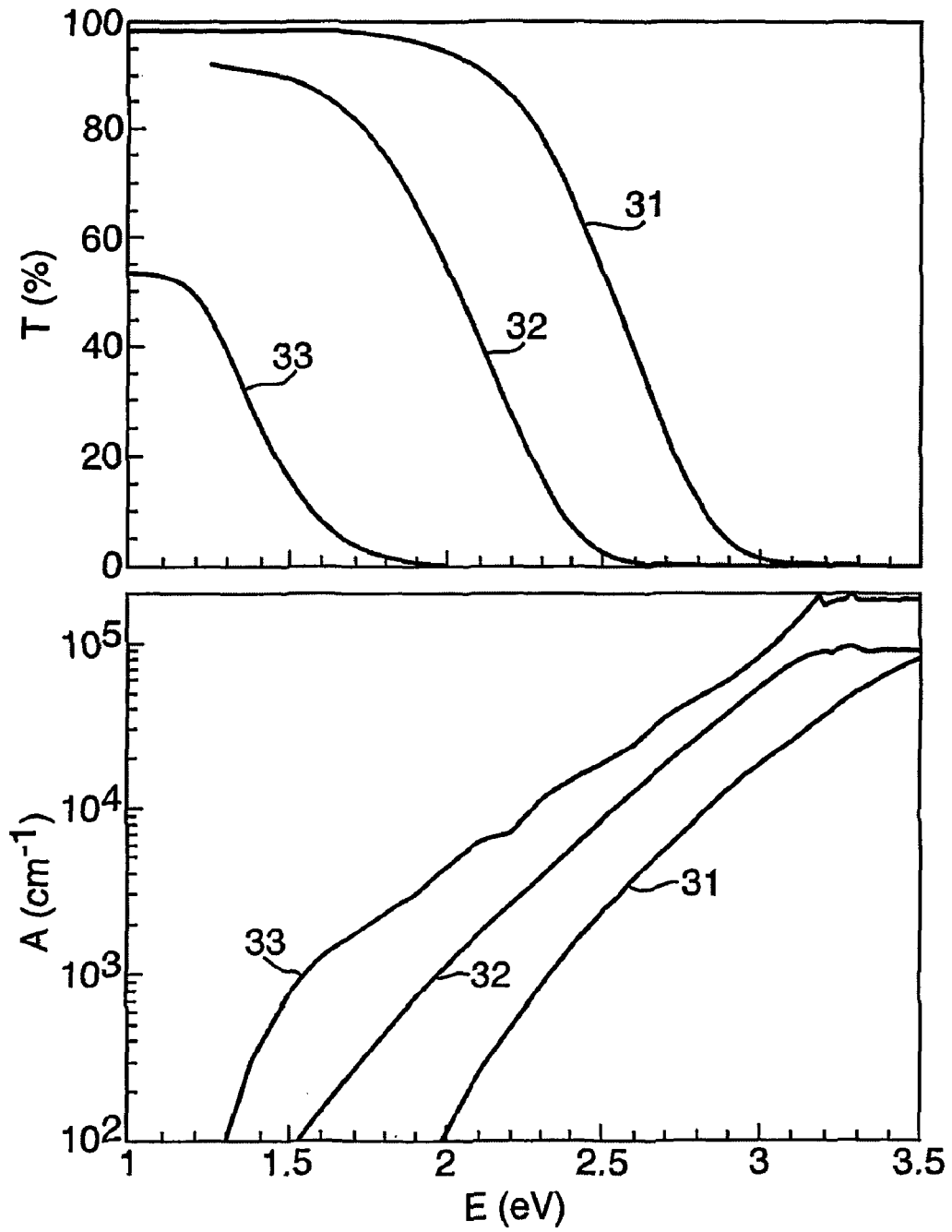
FIG. 3 shows transmission spectra and absorption spectra comparing bulk crystalline silicon with porous silicon with differing degrees of porosity.

A first dermatological composition, according to the invention, may be prepared by the following process:

Step A1

Porous silicon was fabricated by anodising a heavily boron doped CZ silicon wafer with an initial resistivity of 0.01-0.03 $\Omega$cm. The anodisation was carried out in an electrochemical cell, as described in U.S. Pat. No. 5,348,618 containing an electrolyte comprising a 10% solution of hydrofluoric acid in ethanol. An anodisation current with density of 50 mA cm$^{-2}$ was passed for 12 minutes. This produced a 20 µm thick porous silicon layer with a porosity of 90% and a mass density of 0.47 mg cm$^{-2}$.

Step B1

The porous silicon layer may then be detached from the underlying wafer by increasing the current density, for a few seconds, to a sufficiently high value that the silicon at the interface between the porous and bulk crystalline regions is completely dissolved. It was then supercritically dried as described by Canham in Nature, vol. 368, (1994) p 133-135.

Step C1

To produce porous silicon in a particulate form suitable for use in a dermatological composition the detached layer was subjected to ultrasonic agitation in a liquid known to allow good dispersion of silicon powders. Common organic liquids such as alcohols, ketones or aldehydes were found to be suitable. It was then necessary to reduce the size of the silicon particles. This was achieved using a centrifuge as described by Mizuta et al. in Ceramic Bulletin, vol. 61, (1982), p 872-875. The porous silicon particulate layer was suspended in n-propanol and centrifuged at 12000 rpm to remove large agglomerates. The supernatant was then centrifuged at 17000 rpm to give a dispersion of nanoparticulate porous silicon.

Alternatively, the particle size may be reduced by milling, as described by Kerkar et al. in Jn. Am Ceram. Soc., vol 73, (1990), p 2879-2885. The detached layer is mixed with an organic liquid such as trichloroethylene and subjected to attrition milling in a $Si_3N_4$ container using $Si_3N_4$ balls for several hours.

Step D1

After removal of the organic liquid and drying, the powdered porous silicon was suitable for use in a dermatological composition. It was used either without further processing or with one or more beneficial substances.

There are a number of methods by which a beneficial substance may be associated with the silicon particles to be used in the dermatological composition. The beneficial substance may be dissolved or suspended in a suitable solvent, the silicon particles may then be incubated in the resulting solution for a period of time.

The beneficial substance may be deposited on the surface of the implants. If the implants comprise porous silicon, then a solution of the beneficial substance may be introduced into the pores of the porous silicon by capillary action. Similarly if the silicon particles have a cavity then the solution may also be introduced into the cavity by capillary action. If the beneficial substance is a solid but has a sufficiently high vapour pressure at 20 C then it may be sublimed onto the surface of the silicon particles. If a solution or suspension of the beneficial substance can be formed then the substance may be applied to the silicon particles by successive immersion in the solution/suspension followed by freeze drying.

The particle size of the porous silicon was measured by transmission electron microscopy however any other suitable method such as laser Doppler particle size analysis, light scattering or Stokes settling techniques may be used.

Step E1

A dermatological composition was prepared by blending powdered porous silicon with a dermatologically acceptable carrier, such that the percentage of porous silicon comprised about 2% by weight of the composition. If the carrier comprises an oil, then the silicon particles may be sprinkled into the oil with stirring to homogenise the mixture. The oil/porous silicon mixture may then be combined with other components, to form the dermatological composition.

Preparation of a Second Dermatological Composition

A second dermatological composition, according to the invention, may be prepared by the following process:

Step A2

A 0.2 $\Omega$cm p$^-$ CZ Si substrate is anodized in $H_2O$:HF:$C_2H_5OH$ electrolyte, the components of the electrolyte being present in the ratios 1:1:2 by volume. Current density is periodically modulated from 30 mAcm$^{-2}$ to 120 mAcm$^{-2}$ to yield low (corresponding to 30 mAcm$^{-2}$) and high (corresponding to 120 mAcm$^{-2}$) porosity layers. Anodisation in this way results in the formation of a silicon multilayer mirror. By varying the time intervals over which the two current densities flow, the stop band (the spectral region of high reflectivity) of the mirror can be tuned across the visible range and into the ultraviolet.

Typical approximate reflectivities of the as-etched porous silicon mirrors are 99% at 740 nm, 90% at 490 nm, and 50% at 370 nm.

Step B2

A multiplicity of particulate silicon mirrors may then be obtained from the single multilayer mirror film by repeating steps B1 to E1 recited for the first dermatological composition. In this way the multilayer mirror is detached from the silicon substrate, formed into silicon particles (at least some of the particles being a mirror) either ultrasonically or by crushing, combined with one or more beneficial substances, and finally combined with a suitable dermatological carrier.

FIG. 1 shows a number of particulate mirrors 11 that are in contact with the skin 12. Each particulate mirror 11 comprises a plurality of layers of porous silicon (see FIG. 2). Radiation 13, say UV-A radiation, is reflected by the mirrors 11 before the radiation 13 reaches the skin 12. The particulate mirrors 11 form part of a dermatological composition, which also comprises a dermatologically acceptable carrier 14.

FIG. 2 shows one of the particulate mirrors shown in FIG. 1, generally indicated by 13. The particulate mirror 13 comprises a first group of layers 21 and a second group of layers 22, the porosity of the first group 21 differing from that of the second group 22.

Preparation of a Third Dermatological Composition

A third dermatological composition, according to the invention, may be prepared in the following manner:

Step A3

The step A2, given for preparation of the second dermatological composition, is repeated with modulation between 80 mAcm$^{-2}$ to 120 mAcm$^{-2}$. The porous silicon multi-layer mirror may then be detached from the underlying wafer by increasing the current density, for a few seconds, to a sufficiently high value that the silicon at the interface between the porous and bulk crystalline regions is completely dissolved. The mirror is then supercritically dried as described by Canham in Nature, vol. 368, (1994) p 133-135 and thermally oxidised by heating the multilayer mirror in dry oxygen at 950 C for five minutes to yield a porous silicon oxide multilayer mirror. (M Berger et al, Thin Solid Films, Vol 297, p 237-240, 1997).

Step B3

A multiplicity of porous silicon oxide mirrors may then be obtained from the single silicon oxide multilayer mirror by repeating steps C1 to E1 recited for the first dermatological composition. In this way the silicon oxide multilayer mirror is detached from the substrate, formed into particles either ultrasonically or by crushing, combined with one or more beneficial substances, and and finally combined with a suitable dermatological carrier.

The hydrophilicity of the porous silicon oxide mirror may be increased by wet oxidation of the porous silicon at step A3. By increasing the hydrophilicity in this way, aqueous solutions may be used for the ultrasonic and centrifuging processes associated with step C1.

Preparation of a Fourth Dermatological Composition

A fourth dermatological composition, according to the invention, may be prepared in the following manner:

Step A4

A (100) p-type boron doped wafer with resistivity of 0.01 Ωcm is anodised galvanostatically at 37 mAcm$^{-2}$ in a 1:1 by volume mixture of 48% HF:$C_2H_5OH$ for 3 hours in the dark to yield a single 300 μm thick layer of porous silicon. This single layer of porous silicon has an average porosity of 65%. A high current etch of 400 mAcm$^{-2}$ for 5 minutes then releases the porous layer as a free standing film.

Subsequent rinsing with ethanol and excess dry hexane was then carried out without permitting intermediate drying of the wafers. Derivatization was then carried out, using a Lewis acid (EtAlCl$_2$) mediated hydrosilylation to replace the silicon hydride termination of the wafers. Hydrosilylation was carried out with 1 dodecyne and yielded a dodecenyl terminated surface. The Lewis acid mediated hydrosilylation was performed in the following manner:

A hexane solution of the Lewis acid (EtAlCl$_2$) is bought into contact with the surface of the freshly anodized sample of porous silicon (comprising a single layer of uniform porosity). 1 dodecyne is then also placed on the surface of the porous silicon and the consequent reaction is allowed to proceed at an ambient temperature of 20 C for a period of at least 2 hours. The sample is then quenched with THF, followed by $CH_2Cl_2$. The whole process, from the application of the Lewis acid through to the quenching with $CH_2Cl_2$ is performed in an inert atmosphere. The derivatized sample is then rinsed in ethanol and dried under an N$_2$ stream. The resulting surface is capped with a monolayer of dodecenyl groups.

Step B4

A multiplicity of silicon particles, each of which comprises derivatised porous silicon, may then be obtained from the single layer of derivatised porous silicon by repeating steps C1 to E1 recited for the first dermatological composition. In this way the single layer of derivatised porous silicon is detached from the substrate, formed into particles either ultrasonically or by crushing, combined with one or more beneficial substances, and finally combined with a suitable dermatological carrier.

Preparation of a Fifth Dermatological Composition

A fifth dermatological composition, according to the invention, may be prepared by the following process:

A layer of polycrystalline silicon was deposited on a glass substrate by pyrolysis of SiH$_4$ at 0.3 torr, at 600 to 620 C, in a Thermco TMX9000 low pressure chemical vapour deposition hot walled furnace. The glass substrate is then removed by etching in aqueous HF solution to obtain a free standing layer. The polycrystalline layer may then be formed into a multiplicity of silicon particles by ultrasonic treatment or milling as described step C1 and combined with a dermatologically acceptable carrier as described at step E1.

Alternatiely, the multiplicity of polycrystalline silicon particles may be porosified by stain etching prior to combination with the dermatologically acceptable carrier.

Preparation of a Sixth Dermatological Composition

A sixth dermatological composition, according to the invention, may be prepared by the following process:

A mirror comprising multiple layers of polycrystalline silicon may be deposited on a substrate by PECVD of hydrogen diluted SiH$_4$ using electron cyclotron resonance at temperatures less than 200 C (see Kalkan et al J. Appl Phys, Vol 88, p 555-561 (2000)). The microwave power is modulated periodically with time to generate a number of layers of polycrystalline silicon, each layer having a refractive index that differs from those of its adjacent layer(s). The process is performed at a pressure between 5 and 12 mtorr, a silane flow-rate of 2 sccm, and a hydrogen flow rate of 40 sccm.

The polycrystalline mirror may then be formed into a multiplicity of particulate mirrors by ultrasonic treatment or milling as described step C1 and combined with a dermatolocially acceptable carrier as described at step E1.

Transmission Verses Wavelength Characteristics of Porous Silicon

FIG. 3 shows transmission T and absorption coefficient A verses photon energy E spectra for porous and bulk crystalline silicon. Plot 31 corresponds to a 90% porous silicon layer, which effectively screens UV radiation with photon energies of 3.87-3.25 eV (320-400 nm) while allowing transmission of lower energy, longer wavelength visible light. Plot 32 corresponds to 75% porosity porous silicon; a comparison of plots 31 and 32 shows how the transmission properties may be altered by altering the porosity of the porous silicon. Improved UV screening can be achieved by sacrificing some optical transparency and vice versa. The optical characteristics of crystalline bulk silicon, shown by plot 33, displays UV screening capabilities, but shows very poor optical transparency.

Stability of Porous Silicon in Sweat 10 repeat multilayer silicon mirrors, each containing 10 low porosity and 10 high porosity porous silicon layers, were fabricated by anodisation at modulated current density for a total of 156 seconds in 20% ethanoic HF.

Each of the 10 repeat mirrors was immersed in simulated human sweat (SHS) for varying periods of time. The preparation of simulated human sweat was in accordance with ISO standard (3160/2) and is described by J P Randin in J. Biomed. Mater. Res. 22, 649 (1988). The simulated sweat comprises NaCl (20 g/litre), NH$_4$Cl (17.5 g/litre), urea (5 g/litre), acetic acid (2.5 g/litre) and lactic acid (15 g/litre). The pH was adjusted to 5.5 by addition of NaOH.

FIG. 4 shows an SEM image of one of the 10 repeat silicon mirrors prior to immersion in the simulated human sweat.

Figure 5A:
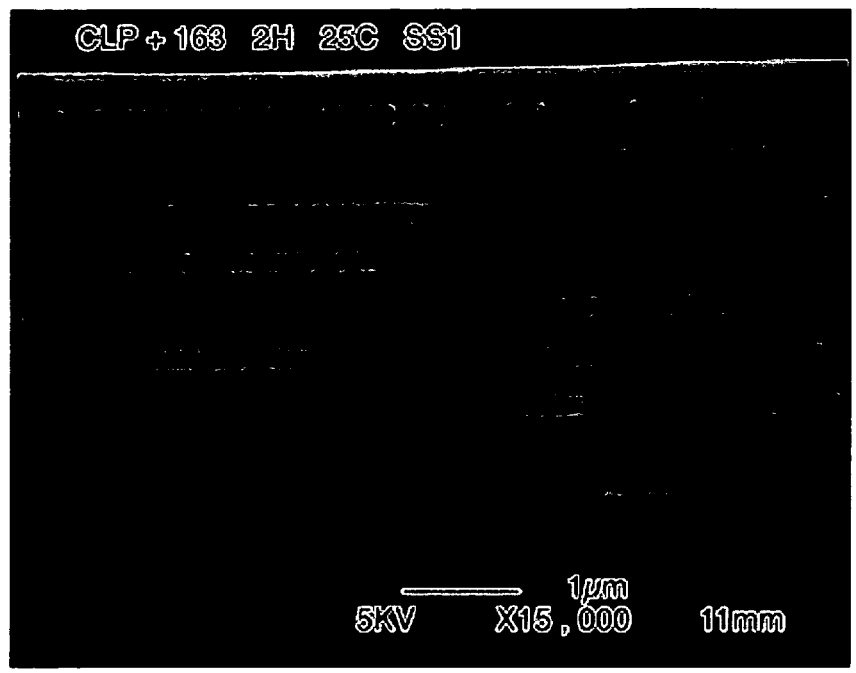
FIG. 5 shows an SEM images of a porous silicon mirror after immersion in simulated human sweat for periods of two, six, and twenty hours.
Figure 5B:
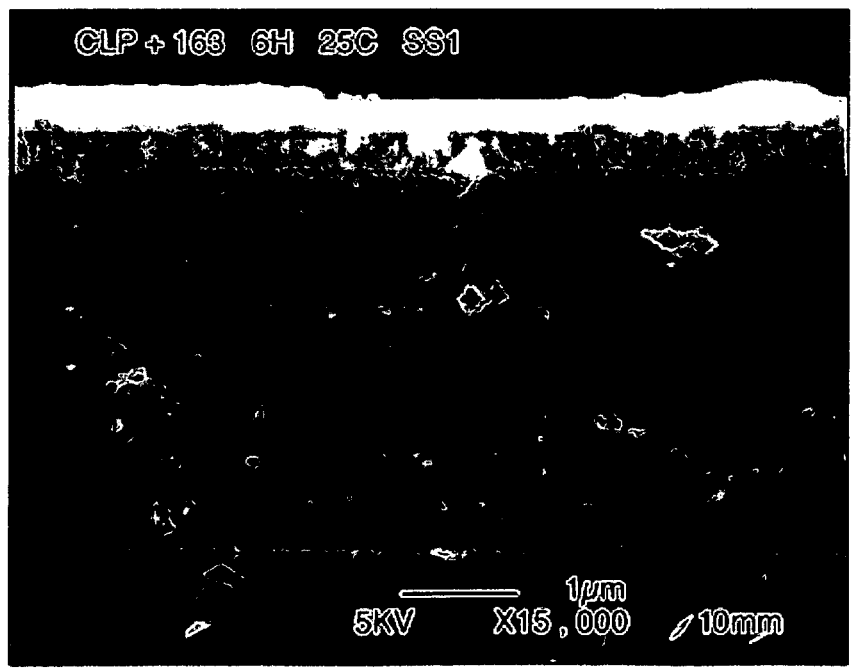
Figure 5C:
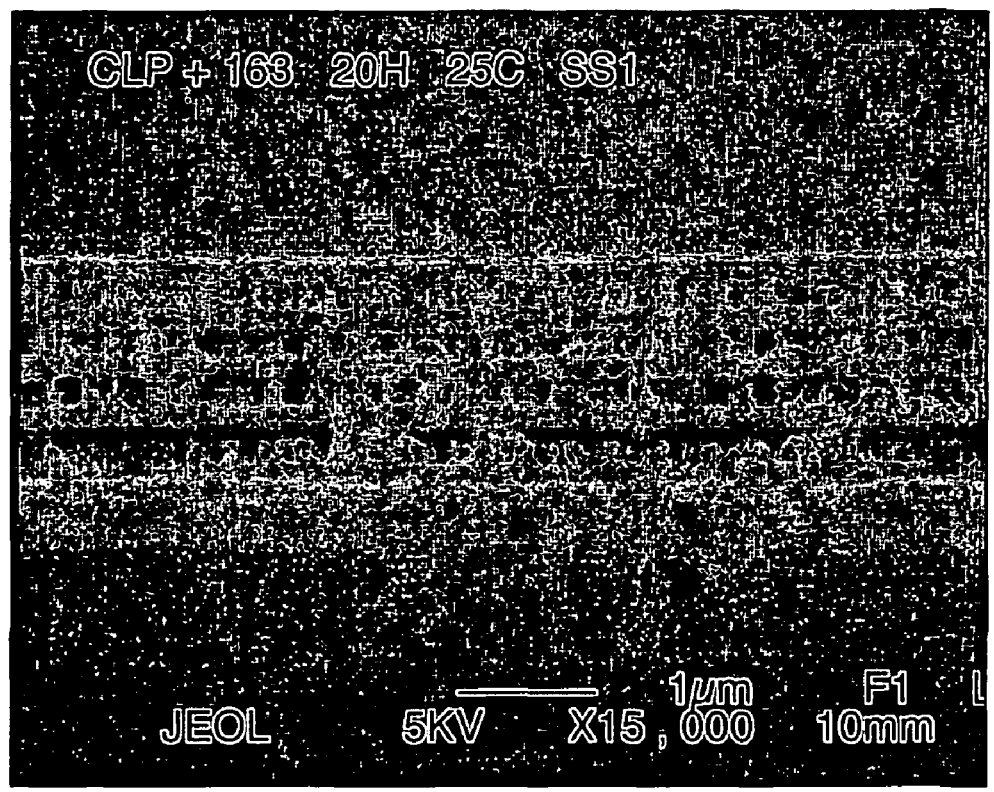

FIG. 5 shows SEM images of one of the ten repeat mirrors after immersion in SHS for a period of 2, 6, and 20 hours at 25 C. After 2 hours (FIG. 5(a)) there is minimal change in thickness, but the topmost high porosity layer has undergone significant attack, after 6 hours (FIG. 5(b)) there are 18 of the 20 layers remaining, whilst after 20 hours (FIG. 5(c)) half of the structure has completely dissolved and the remainder has been affected throughout its depth to become partially delaminated.

Figure 6A:
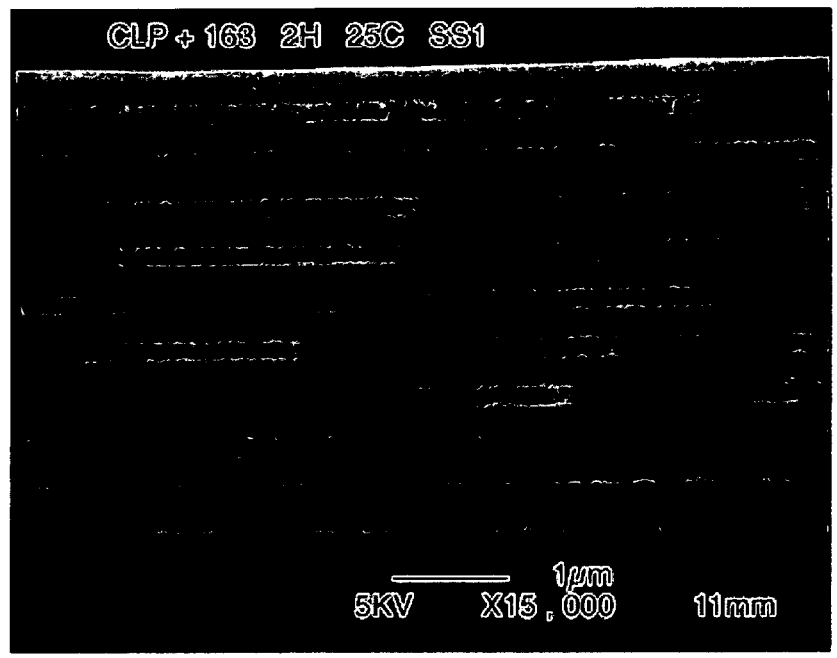
FIG. 6 shows two SEM images, of porous silicon mirrors after immersion in simulated human sweat for the same period of time, the immersion being under different conditions for each mirror.
Figure 6B:
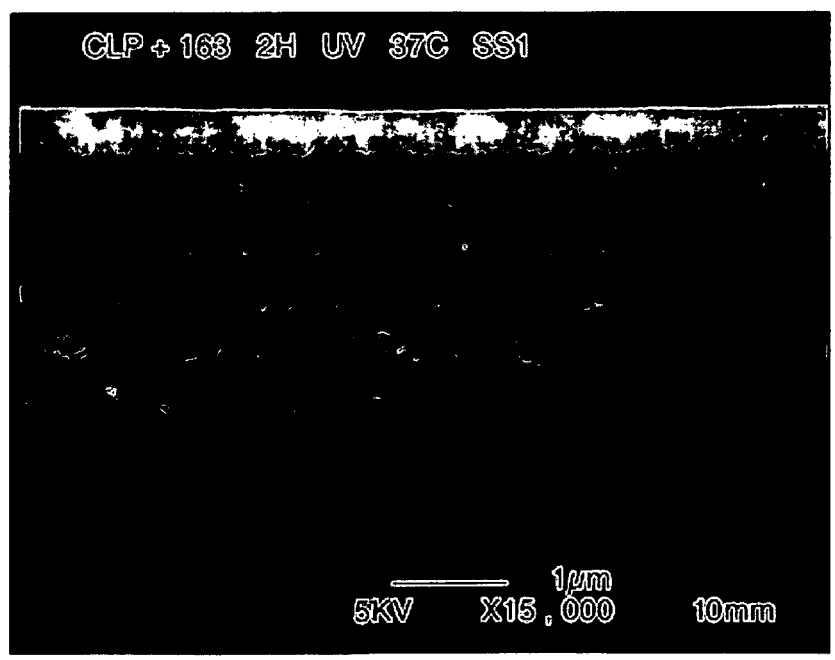

FIG. 6 shows two mirrors, one of which (FIG. 6(a)) has been immersed in SHS at 25 C for a period of 2 hours, and one of which (FIG. 6(b)) has been immersed in SHS at 37 C for 2 hours. The mirror that had been immersed at 37 C was also simultaneously illuminated with; UV radiation (2.5 mWcm$^{-2}$, 365 nm). The illumination with UV radiation at elevated temperatures simulates sunbathing conditions.

Comparison of FIGS. 6(a) and 6(b) shows that illumination with UV and increase in temperature causes an increase in the corrosion rate.

Reflectance Properties of Porous Silicon and Oxidised Porous Silicon

An ultrathick free standing mirror of 300 repeats (600 layers) was fabricated by anodisation in 20% ethanoic HF, at a modulated current density for a total of 1 hour and 8 minutes (0.7 amps for 9 second intervals and 4.55 amps for 4.5 second intervals, the switch between low and high current not being instantaneous).

Viewed at normal incidence, the front face had a red hue, the rear face a vivid green colour. FIG. 7(a) shows the reflectivity spectrum taken from the front face of the intact 150 micron thick film using Ocean Optics S2000 system. The peak in reflectivity at about 650 nm is consistent with its red appearance. The film was then crushed into a powder with a pestal and mortar. The average particle size was approximately 500 microns. FIG. 7(b) shows a reflectivity spectrum from the powder, under conditions where a number of randomly oriented particles contributed to the signal.

A thinner mirror of the same microstructure, fabricated by the same method as that used for the 300 repeat mirror, but having only 100 repeats (200 layers), and still adhered to its silicon substrate, was subjected to partial oxidation.

FIG. 8a shows the reflectance spectrum for the 100 repeat mirror, attached to its substrate. After oxidation the mirror became pale purple in colour and had a blue-shifted reflectance peak shown in FIG. 8b. Further oxidation would shift the reflectance peak out of the visible region and into the near UV region.

Volatile Agents: Loading of and Release from Porous Silicon (A) Lavender Oil

A large flake of a porous silicon membrane, with a dry weight of 8.0±0.1 mg, was immersed at 20 C in 1 ml of Meadows pure concentrated lavender oil (Lavendula Officinalis) for a period of 10 minutes. The flake was then given a brief water rinse. Residual oil on the external surfaces of the flake was then removed by contact with filter paper, and the flake was re-weighed. In its initial as-impregnated state the weight of the flake plus lavender oil was 17.3±0.2 mg, falling by 1 mg in the first 2 minutes but much more gradually thereafter. After 2 hours in air the weight had fallen to 8.6±0.1 mg. The measurements of mass loss were conducted at 20 C and 760 mm Hg.

(B) Tea Tree Oil

A segment of a 100 repeat multilayer mirror attached to its bulk silicon substrate was impregnated with Tea Tree Oil (Melaleica Alternifolia). After pre-warming the layer to 60 C on a hot plate, a drop of concentrated oil was pippetted onto the surface. There was an immediate colour change from green to red and a gradual increase in the diameter of the circular red region of the mirror as the oil droplet spread laterally across the outer surface, in addition to infiltrating the film. Extended application of a stream of dry nitrogen gas to the affected region caused the original green colour to gradually reappear.

Figure 9A:
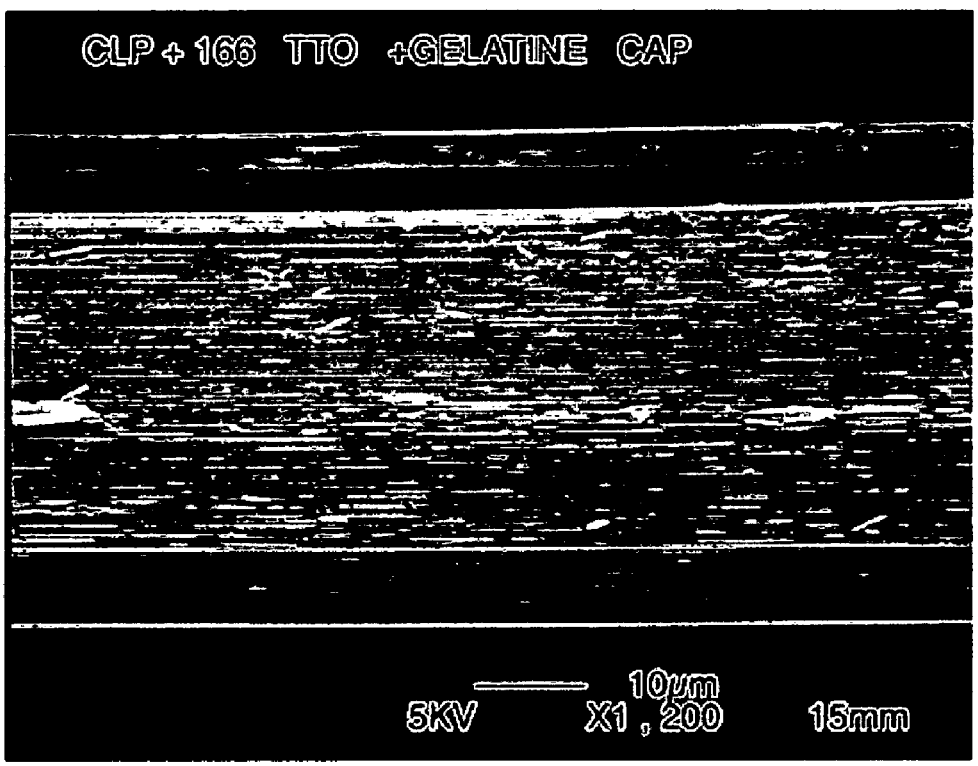
FIG. 9a shows a SEM image of a gelatine coated porous silicon mirror impregnated with Tea Tree Oil.

The initial application of the oil was repeated on another segment, but this time a very thin gelatine film was deposited over the impregnated region to entrap the volatile oil within. This was achieved by warming 2 g of gelatine in 200 ml of water to 45 C and then dipping the segment into this solution and allowing the adsorbed film to solidify by cooling to room temperature in air. The coated segment was found to retain its red colour. FIG. 9a shows an SEM image of the gelatine coated mirror. FIG. 9b shows EDX plots for the top (FIG. 9b(i)), middle (FIG. 9b(ii)), and bottom (FIG. 9b(iii)) of the layer of porous silicon containing the Tea Tree Oil and capped with gelatine. The EDX plots show that the oil (indicated by the carbon and oxygen peaks) has penetrated throughout the layer of porous silicon.

Alternative Methods of Impregnation

A sample of porous silicon, either attached to or detached from a bulk crystalline silicon substrate, may be disposed in a sealed container above a volatile liquid. The vapour pressure within the porous silicon may slowly be increased by heating the volatile material between its melting point and its boiling point. This appraoch may be of value for volatile liquids that do not wet porous silicon or which are prone to solidification on the pore walls.

Preparation of Porous Polycrystalline Silicon

Figure 10A:
FIG. 10a shows an SEM image of a polycrystalline layer deposited on a silica substrate.
Figure 10B:
FIGS. 10b and 10c show SEM images of porosified polycrystalline layers.
Figure 10C:

FIG. 10a shows a SEM image of a polycrystalline film of silicon, deposited onto silica by thermal decomposition of silane at 620 C in a LPCVD reactor. Segments were subjected to a stain etch in a 50:1 mixture of 40 wt % HF and 70% nitric acid respectively. After 15 seconds, about half the layer was porosified (as shown in the SEM image of FIG. 10(b); after 30 seconds the electrolyte had penetrated through the full thickness of the layer and has started to create voids in the underlying oxide (FIG. 10(c)).

The use of porous polycrystalline silicon in dermatological compositions is of value, since it is much less expensive to fabricate than porous silicon derived from bulk crystalline silicon.

The invention claimed is:

1. A method of protecting the skin of a human or animal from UV radiation comprising the step of topically applying a dermatological composition comprising a plurality of particles comprising porous silicon having a particle size in a range of 0.01 to 250 µm.

2. A method according to claim 1 wherein the composition further comprises a dermatologically acceptable carrier.

3. A method according to claim 1 wherein the porous silicon is resorbable.

4. A method according to claim 1 wherein the composition comprises porous silicon having a monomolecular or monoatomic layer that is chemically bonded to at least part of the surface of the pores of the porous silicon.

5. A method according to clam 1 wherein the composition comprises a plurality of mirrors made from a plurality of layers of porous silicon, each mirror comprising a plurality of layers, each layer comprising porous silicon.

6. A method according to claim 5 wherein the composition comprises a plurality of groups of mirrors, each group reflecting radiation over a wavelength range that differs from that of the other groups.

7. A method according to claim 1 wherein the composition further comprises at least one beneficial substance selected from the group consisting of a biological material, a genetic material, a radioactive material, an antibacterial and a luminescent material.

* * * * *